United States Patent [19]

Drauz et al.

[11] Patent Number: 5,723,667
[45] Date of Patent: Mar. 3, 1998

[54] METHOD OF PRODUCING OPTICALLY ACTIVE TERT-LEUCINOL AND ITS USE

[75] Inventors: Karlheinz Drauz, Freigericht; Wilfried Jahn, Gelnhausen; Michael Schwarm, Alzenau, all of Germany

[73] Assignee: Degussa Aktiengesellschaft, Germany

[21] Appl. No.: 603,553

[22] Filed: Feb. 21, 1996

[30] Foreign Application Priority Data

Feb. 21, 1995 [DE] Germany ................. 195 05 994.8

[51] Int. Cl.⁶ .................... C07C 209/88; C07C 215/08; C07B 57/00
[52] U.S. Cl. ..................... 564/302; 564/303; 564/503
[58] Field of Search ................. 564/302, 303, 564/503

[56] References Cited

U.S. PATENT DOCUMENTS

| | | | |
|---|---|---|---|
| 3,116,332 | 12/1963 | Sullivan | 564/302 |
| 3,553,257 | 1/1971 | Halmos et al. | 564/302 |
| 3,970,700 | 7/1976 | Nagase et al. | 564/302 |
| 4,259,521 | 3/1981 | Kazan et al. | 562/401 |
| 4,330,484 | 5/1982 | Berning et al. | 564/303 |
| 4,340,751 | 7/1982 | Nohira et al. | 562/401 |
| 5,442,117 | 8/1995 | Stahly et al. | 564/304 |
| 5,536,879 | 7/1996 | Antons et al. | 564/503 |

FOREIGN PATENT DOCUMENTS

| | | |
|---|---|---|
| 036 265 | 9/1981 | European Pat. Off. |
| 1 471 838 | 4/1977 | United Kingdom . |

OTHER PUBLICATIONS

Derwent Publications Ltd., JP-A-56-095 149, London, GB Database WPI Week 8137 (1981).

Drauz, et al., Synthesis of (R)-tert-Leucinol by Classical Resolution of the Racemic Mixture, Chemistry A European Journal, vol. 1, pp. 538-540, Nov. 1995.

McKennon et al., A Convenient Reduction of Amino Acids and Their Derivatives, Journal of Organic Chemistry, vol. 58, pp. 3568–3571, Jun. 1993.

Abiko et al., An Improved, Convenient procedure for Reduction of Amino Acids to Aminoalchols, Tetrahedron Letters, vol. 33, pp. 5517–5518, 1992.

Nishiyama et al., Chiral and C2-Symmetrical .... vol. 8, pp. 846–850, Organometallics, Jan. 1989.

Primary Examiner—Deborah Lambkin
Attorney, Agent, or Firm—Cushman Darby & Cushman IP Group of Pillsbury Madison & Sutro

[57] ABSTRACT

A method of producing optically active tert-leucinol (formula I) of high enantiomeric purity

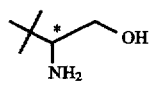

(I)

by converting racemic (RS)-tert-leucinol into a diastereomeric salt pair by reaction with an optically active acid, removing the salt pair from solution by fractionated crystallization and separating therefrom the optically active acid to release the optically active tert-leucinol from the salt. The optically active acid used is an N-acylated tert-leucine of general formula VIII:

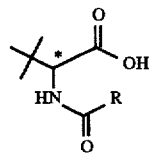

(VIII)

in which R can be hydrogen or an alkyl-, arylalkyl- or aryl group with up to 20 C atoms and * signifies a chirality center.

20 Claims, No Drawings

METHOD OF PRODUCING OPTICALLY ACTIVE TERT-LEUCINOL AND ITS USE

BACKGROUND OF THE INVENTION

1. Field of the Invention

The invention is relative to a method of producing optically active tert-leucinol (formula I)

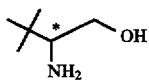
(I)

in which * signifies a chirality center, in which method racemic (RS)-tert-leucinol is converted by reaction with an optically active acid into a diastereomeric salt pair, the latter is then crystallized in a fractionated manner (cf. p. 5, l. 1.63 below) and the optically active tert-leucinol is released therefrom by separating off the optically active acid and optionally isolated in reagent, and to its use for producing derivatives.

2. Background Information

Optically active tert-leucinol and its derivatives find broad application in asymmetric synthesis, in which reactions are carried out with a prochiral precursor. Because the tert-butyl group is especially sterically demanding and exerts a directing influence on the reactions taking place on the prochiral molecules or molecule groups, these reactions take place in the presence of an optically active tert-leucinol derivative with high diastereo- or enantioselectivity. Examples of such derivatives with which a plurality of asymmetric reactions can be carried out are 4-tert-butyl-2-oxazolidinone (formula II) (D. A. Evans, K. T. Chapman, J. Bisaha, J. Am. Chem. Soc. 1988, 110, 1238), oxazolines (formula III) (A. N. Hulme, A. I. Meyers, J. Org. Chem. 1994, 59, 952) and bicyclic lactams (formula IV) (D. Romo, A. I. Meyers, J. Org. Chem. 1992, 57, 6265)

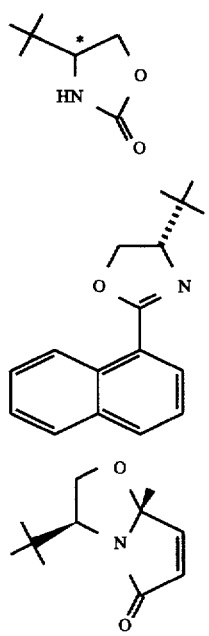

(II)

(III)

(IV)

or ligands for producing chiral catalysts such as mercaptophenyloxazoline (formula V) (Q.-L. Zhou, A. Pfaltz, Tetrahedron Lett. 1993, 34, 7725), bisoxazoline (formula VI) (D. A. Evans, S. J. Miller, T. Lectka, J. Am. Chem. Soc. 1993, 115, 6460) or bis(oxazolinyl)pyridine (formula VII) (H. Hishiyama, H. Sakaguchi, T. Nakamura, M. Morihata, M. Kondo, K. Itoh, Organometallics 1989, 8, 846).

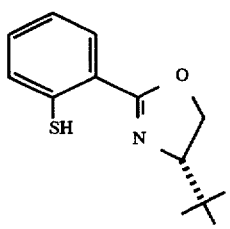
(V)

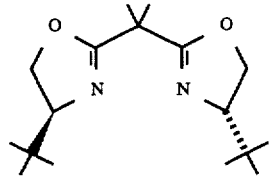
(VI)

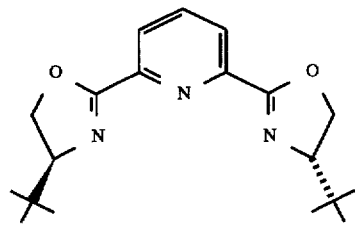
(VII)

An insertion of an optically active tert-leucinol or one of its derivatives into a pharmaceutically effective substance which could have, for example, a peptide-like structure is also conceivable.

One problem which limits the use of optically active tert-leucinol for the above-described purposes is obtainability, which has often been poor in the past. Optically active tert-leucinol was previously produced by reduction of the corresponding, optically active tert-leucine with one of the reagents common for the reduction of amino acids (H. Nishiyama, H. Sakaguchi, T. Nakamura, M. Morihata, M. Kondo, K. Itoh, Organometallics 1989, 8, 846; A. Abiko, S. Masamune, Tetrahedron Lett. 1992, 33, 5517; M. J. McKennon, A. I. Meyers, K. Drauz, M. Schwarm, J. Org. Chem. 1993, 58, 3568). However, this presupposes that the particular tert-leucine is available in an optically pure form.

(S)-tert-leucine is readily available enzymatically in industrial amounts via a transamination (EP 0,248,357 A2) or, in particular, a reductive amination of trimethylpyruvic acid (A. S. Bommarius, K. Drauz, W. Hummel, M.-R. Kula, C. Wandrey, Biocatalysis 1994, 10, 37; U. Kragl, D. Vasic-Racki, C. Wandrey, Chem. Ing. Tech. 1992, 64, 499). In contrast thereto, (R)-tert-leucine can be obtained only with difficulty via expensive chemical or enzymatic racemate splittings (J. Viret, H. Patzelt, A. Collet, Tetrahedron Lett. 1986, 27, 5865 and literature cited there), particularly also because the production of pure, racemic (RS)-tert-leucine is associated with relatively great expense (F. Knoop, G. Landmann, Z. Physiol. Chem. 1914, 89, 57).

Furthermore, it is generally known to persons of skill in the art that racemic compounds can be reacted, to the extent available, for splitting in various solvents with optically active acids in order to produce diastereomeric salt pairs and the latter separated by fractionated crystallization. However, even though this method is generally known it cannot be predicted in a given instance whether a crystalline salt is obtainable at all and if so, with which acid; and which particular enantiomer of the racemic mixture can be separated with which particular enantiomer of the acid as salt. Moreover, for reasons of economy the optically active acid should be readily available and as recyclable as possible.

The second point is especially important for ecological reasons since otherwise a considerable amount of waste is produced.

SUMMARY OF THE INVENTION

In view of the state of the art indicated above, it is an object of the invention to provide a method of producing optically active tert-leucinol and its derivatives in a high yield with high optical purity with respect to the enantiomers without having to reduce optically active tert-leucine as precursor.

It is a further object of the invention to provide a method for producing (R)-tert-leucinol, which could only be obtained up to the present with difficulty, and its derivatives.

These problems and others not individually cited are solved by a method with the features detailed in claim 1. Advantageous modifications in the method of the invention constitute subject matter of the method claims dependent on claim 1.

Preferred usages are placed under protection in the claims of the corresponding category.

Furthermore, novel substances obtainable in the method of the invention as product or intermediate product constitute subject matter of claim 21.

As a result of the fact that an N-acylated tert-leucine of general formula VIII is used as optically active acid

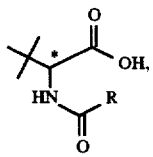

(VIII)

in which R can be hydrogen or an alkyl-, arylalkyl- or aryl group with up to 20 C atoms optionally substituted with heteroatoms, or containing the latter, and * signifies a chirality center, optically active tert-leucinol and its derivatives are readily, reliably and economically obtainable in high enantiomeric purity both in the (R) and in the (S) configuration.

Based on the foregoing, it was not predictable or to be expected in any way that optically active N-acylated derivatives of (R)- or (S)-tert leucine, which can be readily produced in a good yield according to generally known methods by reacting (R)- or (S)-tert-leucine with an ester, acid anhydride or acid chloride, would form salts with tert-leucinol in which one of the two enantiomers is enriched to a greater or lesser extent. Compounds of formula VIII which can be used with success in the invention include, for example, N-formyl-, N-benzoyl- and N-(2-naphthoyl)-tert-leucine. In particular, the (S) enantiomers can be especially advantageously used in the method of the invention.

In a preferred embodiment of the invention an optically active N-formyl-tert-leucine is used as optically active acid.

Thus, a salt with a R/S-tert-leucinol ratio of 93.9:6.1 was isolated with N-formyl-(S)-tert-leucine from isopropanol in 45% yield. Recrystallization improved the purity to 98.6:1.4.

Optically active tert-leucine derivatives, preferably (S)-tert-leucine derivatives, which were protected on the nitrogen with rather large aroyl groups, preferably formed salts according to the invention during the reaction with (RS)-tert-leucinol, and an optically active form predominated in these salts. In the instance where (S)-tert-leucine derivatives were used, (R)-tert-leucinol predominated in the examples analyzed.

The resolution of racemates of (RS)-tert-leucinol can be carried out in a particularly advantageous manner with N-(2-naphthoyl)-(R)- or -(S)-tert-leucine.

Thus, according to a method of the invention, racemic (RS)-tert-leucinol is split by reaction with optically active acids into the enantiomers, which are first obtained in the form of salts with the optically active acids. The optically active tert-leucinol (formula I) can be released from these salts in a generally known manner; this tert-leucinol can either be isolated in pure form or reacted in situ to produce further derivatives like the above-described compounds II–VII. Both the (S)- and in particular the (R)-tert-leucinol, which has been very difficult to obtain up to the present, and their derivatives, can be readily obtained in high optical purity according to this method.

The reaction of the racemic (RS)-tert-leucinol with the compound of general formula VIII is preferably carried out in an organic solvent. Generally, solvents familiar to a person of ordinary skill in the art and useful in the resolution of racemates such as alcohols, esters, ethers, ketones or hydrocarbons can be considered for this purpose. Alcohols with 1–6 C atoms such as methanol, ethanol, propanol, isopropanol, n-butanol or isobutanol are especially advantageous. The use of isopropanol proved to be particularly favorable.

It is preferable to proceed in a manner whereby the racemic (RS)-tert-leucinol is dissolved together with the derivative of the optically active acid in the solvent with heating, preferably using only 0.5 equivalents of the optically active acid relative to the racemic amino alcohol. The mixture is then cooled under agitation, during which a salt of the diastereomeric salt pair crystallizes out first and the other enantiomer of the tert-leucinol remains enriched in the mother liquor.

The desired, optically active tert-leucinol can be isolated from the salt which has crystallized out in any manner familiar to a person of ordinary skill in the art. In a preferred embodiment of the invention, the optically active tert-leucinol is separated from a salt with the optically active acid by reacting the salt with an aqueous solution of a strong acid and recovering the optically active acid by filtering off or by extraction with an organic solvent. The aqueous solution is then alkalinized and the optically active tert-leucinol extracted with an organic solvent and optionally isolated by evaporation to low bulk, distillation, chromatography or recrystallization of an acidic salt and further purified.

Thus, the optically active acid is released from the salt by the addition of a strong acid such as, for example, hydrochloric or sulfuric acid, and suitably separated; and the optically active tert-leucinol is subsequentlly isolated in a suitable manner after alkalinizing the aqueous solution. This also recovers the optically active acid in an advantageous manner.

According to the invention, aromatic hydrocarbons are preferred as extraction agents for optically active tert-leucinol. They include, inter alia, toluene, xylenes and cumene. Toluene is especially preferred. However, other organic solvents which are non-miscible with water can also be used.

The optical antipode of the optically active tert-leucinol compound obtainable with the above-described method can be obtained in an especially favorable manner within the framework of the invention from the mother liquor of the crystallization. Since the mother liquor is heavily depleted due to the separation of the salt of one enantiomer, the tert-leucinol remaining in the mother liquor and accessible to recovery is heavily enriched with the Other enantiomer. This enantiomer is obtainable in especially high optical purity from the recovered tert-leucinol by reaction with a suitable, optically active acid.

For example, the resolution of racemates can be carried out quite advantageously in the invention with N-(2-naphthoyl)-(S)-tert-leucine by reaction in a solvent. The prefered solvent is an alcohol, especially isopropanol. For this the racemic (RS)-tert-leucinol as well as the N-(2-naphthoyl)-(S)-tert-leucine are dissolved in the alcohol with heating. The mixture is then cooled off in a controlled manner under agitation during which the salt of (R)-tert-leucinol and N-(2-naphthoyl)-(S)-tert-leucine crystallizes out. The yield after recrystallization for this preferred variant of the invention was, for example, 70% with an R/S-tert-leucinol ratio of 98.7:1.3. The tert-leucinol, which is now heavily enriched with the (S) enantiomer, can then be isolated from the mother liquor of this reaction by concentration, taking up in an aqueous acid, filtering off the N-(2-naphthoyl)-(S)-tert-leucine, alkalinizing the filtrate and extracting with an organic solvent. If the extracted tert-leucinol is dissolved warm in isopropanol and reacted with (S)-mandelic acid, a salt of (S)-tert-leucinol and (S)-mandelic acid separates during cooling which displayed an R/S ratio of 1.0:99.0 in an exemplary test after two recrystallizations. The yield was 63% thereafter relative to the (S)-tert-leucinol present in the original racemic (RS)-tert-leucinol.

In this manner salts of the (S)- and also especially of the (R)-tert-leucinol, which could only be obtained with difficulty in the past, are obtainable from racemic (RS)-tert-leucinol and have an especially high optical purity. As already mentioned, the amino alcohol can be isolated from these salts if necessary. This can be performed in a known manner by suspending or dissolving the salt in water and compounding this mixture with a strong acid in order to release the optically active acid, which can then be crystallized out or extracted. For example, the N-(2-naphthoyl)-(S)-tert-leucine can be recovered thereby in 99% yield, which emphasizes the advantageous suitability of this compound for a resolution of racemates. The aqueous phase is then alkalinized, the optically active tert-leucinol extracted from it with an organic solvent and optionally purified further by distillation. (R)-tert-leucinol was isolated in this manner with a yield of 55% relative to the racemic (RS)-tert-leucinol and of 78% relative to the salt with N-(2-naphthoyl)-(S)-tert-leucine, and the R/S-tert-leucinol ratio of 98.7:1.3 coincided exactly with the value determined for the salt. The amount of rotation of the product (−38.1° (c=2, EtOH)) exceeded even the values indicated in the literature for (S)-tert-leucinol (+37.24° (c=1.02, EtOH) (Nishiyama, Sakaguchi, Nakamura, Morihata, Kondo, Itoh, 1989; +37° (c=1, EtOH) (McKennon, Meyers, Drauz, Schwarm, 1993)), with the sign of course being opposite.

This method is presented again in the following in schematic fashion:

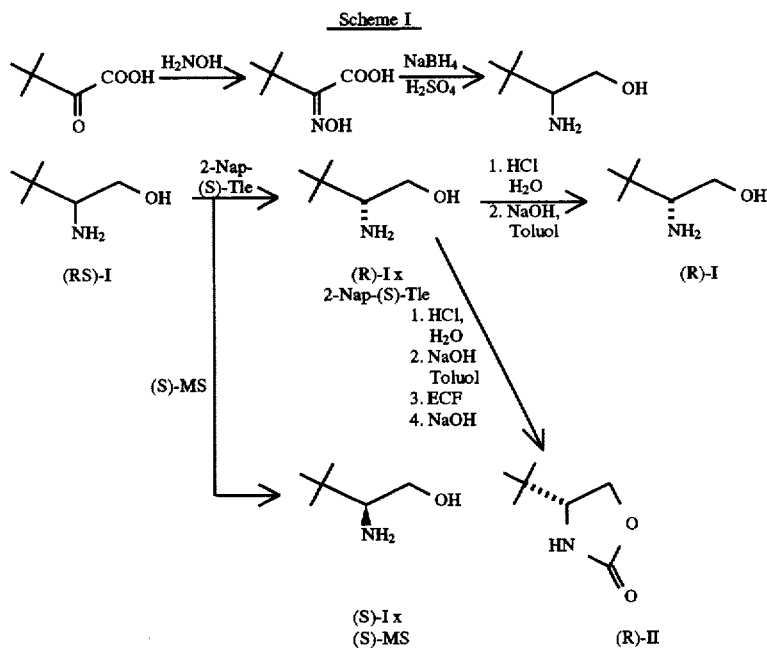

key: Toluol=toluene
2-Nap-(S)-Tle=N-(2-naphthoyl)-(S)-tert-leucine (S)-MS=(S)-mandelic acid ECF=ethylchloroformate The racemic (RS)-tert-leucinol required as starting material can be produced in principle by the reduction of (RS)-tert-leucine in accordance with the methods known for the reduction of amino acids. However, it was surprisingly found that (RS)-tert-leucinol is also obtainable without difficulty in good yield by the reduction of the readily accessible oxime of trimethylpyruvic acid. The latter can be produced in a known, very simple manner (Knoop, Landmann, 1914) by reacting trimethylpyruvic acid or one of its salts with hydroxylamine hydrochloride in water and crystallizes out of the reaction solution directly in good yield and high purity, in contrast to the expensive extractive workup cited in the literature.

The reduction of the oxime of trimethylpyruvic acid is carried out in accordance with the invention with an alkali boron hydride such as lithium- or sodium boron hydride (preferably the economical sodium boron hydride) and with an activator such as hydrochloric or sulfuric acid in a solvent. The solvent is advantageously an ether, especially 1,2-dimethoxyethane or tetrahydrofurane. These reagents are already known for the reduction of amino acids (Abiko, Masamune 1992; McKennon, Meyers, Drauz, Schwarm, 1993). It advantageously happens that they are also very well suited for the reduction of trimethylpyruvic acid oxime to (RS)-tert-leucinol; the reaction can be carried out in principle in a broad temperature range from approximately −20° C. to the boiling temperature of the solvent used. The reaction is preferably carried out in such a manner that the reagents are placed together at approximately room temperature, optionally under cooling, and is then completed by heating to temperatures of up to approximately 75° C. This was especially surprising for the reason that the agent with reducing action is obviously diborane produced in situ (Abiko, Masamune, 1992); however, it has been pointed out elsewhere (H. Feuer, D. M. Braunstein, *J. Org. Chem.* 1969, 34, 1817) that oximes were only able to be reduced by diborane at an elevated temperature of 105°–110° C. in diglyme-THF [diglycol methyl ether THF] to the corresponding amines whereas no reaction or only reduction to the hydroxylamines was observed at lower temperatures. In contrast thereto, such high temperatures and the use of the expensive solvent diglyme which renders the workup difficult can be eliminated for the.. reduction of trimethylpyruvic acid oxime to (RS)-tert-leucinol in accordance with the invention. 71% (RS)-tert-leucinol was obtained in this manner after distillation in an, exemplary test.

The above-named compounds II–VII or further derivatives of optically active tert-leucinol can then be produced in a known manner from the optically active tert-leucinol isolated in accordance with the invention.

However, it is also possible to directly produce one of compounds II–VII or further derivatives of optically active tert-leucinol from the salt of optically active tert-leucinol with an optically active acid without having to isolate the optically active tert-leucinol in substance. Thus, the (R) isomer of the oxazolidinone II can be directly produced, for example from the salt of (R)-tert-leucinol and N-(2-naphthoyl)-(S)-tert-leucine, which simultaneously demonstrates the advantageous utility of the (R)-tert-leucinol obtained by the resolution of racemates in accordance with the invention for producing this enantiomer of II, which was obtainable only with difficulty in the past.

By way of example, the synthesis of (R)-II was carried out in such a manner that at first a solution of the amino alcohol was produced in an organic solvent by extraction as described above. In principle all organic solvents which form a two-phase system with water and in which the optically active tert-leucinol is soluble (at elevated temperature if necessary), for example, ethers, esters, chlorinated hydrocarbons or aromatic, alicyclic or aliphatic hydrocarbons, are suitable for this. Those preferred are ones in which the subsequent acylation of the amino alcohol and the cyclization to the oxazolidinone can take place without changing the solvent, e.g. aromatic hydrocarbons. Toluene is especially preferred. The amino alcohol dissolved in the organic solvent is acylated in a generally known manner with phosgene or a phosgene derivative such as a chloroformic acid ester or a dialkyl carbonate on the nitrogen, during which the pH is optionally maintained by the addition of sodium hydroxide solution in a range of 6–12, preferably 7–8.5. Chloroformic acid esters are especially preferred as acylation agents as they can be readily handled and are economical. The N-acylated, optically active tert-leucinol is then cyclized, optionally under the addition of a base and optionally at elevated temperature, to the optically active oxazolidinone II. Economical sodium hydroxide is preferred as base; however, other inorganic or organic bases are also suitable. The reaction is preferably carried out in a range from room temperature to the boiling temperature of the solvent used. In the exemplary test the desired (R)-4-tert-butyl-2-oxazolidinone ((R)-II) was isolated with 80% yield. The amount of rotation (+18.8°, c=1, EtOH) corresponded exactly in magnitude to that of a sample of the (S) enantiomer (−18.8°, c=1, EtOH) produced for comparison from (S)-tert-leucine by reduction, acylation and cyclization. The R/S ratio for the (R)-II produced in accordance with the invention was >99.0:<1.0, that is, the amount of the (S) enantiomer was clearly below the detection limit. Thus, an additional purification took place by means of the crystallization of (R)-II so that the amount of the false enantiomer in the product was again clearly lowered in comparison to the educt (1.3% (S)-tert-leucinol).

On the whole, the methods of the invention open a novel, especially simple access to optically active tert-leucinol and its derivatives, making it in particular possible to obtain (R)-tert-leucinol, which could only be produced with difficulty in the past, in an advantageous manner, as well as its derivatives. The method is explained further by the following examples:

DETAILED DESCRIPTION OF THE INVENTION

EXAMPLE 1

Production of trimethylpyruvic acid oxime 163 g (1 mole) 93.5% trimethylpyruvic acid sodium salt and 69.5 g (1 mole) hydroxylamine hydrochloride were dissolved at 40° C. in 450 ml water. The product crystallized out during slow cooling under agitation. After 1.5 h agitation in an ice bath the crystals were filtered off, washed with 150 ml ice water, dried in a vacuum at 60° C., and then further dried in a vacuum desiccator over phosphorus pentaoxide to constant weight. 117.8 g trimethylpyruvic acid oxime (81% yield) in the form of colorless crystals were obtained.

Melting range: 120°–122° C. (decomposition) (lit.: 121° C. (Knoop, Landmann, 1914)) $C_6H_{11}NO_3$ calc. C 49.64 H 7.64 N 9.65 (145.16) obs. C 49.75 H 7.89 N 9.71

EXAMPLE 2

Production of (RS)-tert-leucinol 120 ml (2.25 moles) conc. sulfuric acid were added dropwise under agitation at a maximum of 15° C. to 480 ml of 1,2-dimethoxyethane (DME).

218 g (1.5 moles) trimethylpyruvic acid oxime were added in portions to an agitated suspension of 171 g (4.5 moles) sodium boron hydride in 1500 ml DME at 10°–30° C., during which a vigorous development of gas began. Then the sulfuric acid-DME solution was added dropwise under ice cooling within 2.5 h, during which the temperature rose from 10° C. to 40° C. and, after cooling was stopped, to 55° C. The mixture was then heated to 70° C., cooled and allowed to stand for 2 days at room temperature.

In order to destroy excess boron hydride, first 200 ml methanol was added dropwise at 20°–55° C. and then 100 ml water was added, during which the temperature rose to 60° C. A vigorous development of gas was observed during the entire hydrolysis procedure. The mixture was then evaporated in a vacuum to a thin paste and after the addition of a further 500 ml ice water the organic solvent mixture was distilled off. After addition of a further 600 ml water, 200 ml conc. hydrochloric acid was added dropwise at 25° C., during which the temperature rose to 35° C. and a vigorous development of gas began again.

After 15 min of subsequent agitation the suspension was compounded with 1500 ml toluene and made alkaline with 300 ml of 50% sodium hydroxide solution. The temperature, which rose during this process to 55° C., was elevated further to 70° C., whereupon the toluene phase was separated. The aqueous phase was extracted twice more with 1 l toluene, each time at 70° C. The combined toluene phases were then treated with Celite, filtered and evaporated to dryness in a vacuum, yielding 158 g of a yellowish oil which crystallized in the cold. Distillation yielded 125.1 g (RS)-tert-leucinol (71% yield) as a colorless liquid which solidified at room temperature. A $^1$H-NMR spectrum corroborated the suggested structure.

Boiling range: 86°–95° C./13 mbar Melting range: 34°–35° C. $C_6H_{15}NO$ calc. C 61.49 H 12.90 N 11.95 117.19 obs. C 61.10 H 13.15 N 11.88

EXAMPLE 3

Production of N-(2-naphthoyl)-(S)-tert-leucine

A solution of 152.4 g (0.80 mole) 2-naphthoyl chloride in 200 ml THF was added to a solution of 110 g (0.834 mole) (S)-tert-leucine in 1600 ml water under agitation over 5 min, during which the pH was maintained between 7.1 and 7.6 by the simultaneous addition of 5 M sodium hydroxide solution (a total of about 330 ml). The temperature was lowered from 28° C. initially to 22° C. and the batch agitated a total of 1.5 hours longer until the pH no longer changed. The THF was then distilled off in a rotary evaporator, the thin crystal suspension produced was agitated 1 h at 10° C. and then filtered in order to separate off a crystallized byproduct (15.4 g after drying).

The filtrate was then adjusted to pH 2.0 with semi-concentrated hydrochloric acid, whereupon the reaction product separated in fine crystals. The thick suspension was tempered by the addition of ice to about 10° C., agitated 30 min more and filtered. After washing with water and drying in a vacuum at 50° C., 204 g solid were isolated which, however, still contained a byproduct after TLC analysis. (diethylether/methanol =10/2). The product was therefore recrystallized out of 2500 ml toluene and again out of 3000 ml toluene, whereupon after drying in a vacuum at 50° C., 169.4 g N-(2-naphthoyl)-(S)-tert-leucine (74% yield) were isolated in the form of colorless crystals. The product was now homogeneous according to thin-layer chromatography and its structure was corroborated by an $^1$H-NMR spectrum. The analyses showed that the product obtained in this manner still contained 3.12% water. The compound was able to be obtained water-free and analytically characterized after more rigorous drying (see example 6).

EXAMPLE 4

Reaction of (RS)-tert-leucinol with N-(2-naphthoyl)-(S)-tert-leucine 175.8 g (1.5 moles) (RS)-tert-leucinol and 214.0 g (0.75 mole) N-(2-naphthoyl)-(S)-tert-leucine were dissolved in 4500 ml isopropanol at 53° C. A few crystals re-formed spontaneously at this temperature. The mixture was cooled under slow agitation within 6 h from 53° C. to 39° C., then overnight to 24° C. and then in an ice/water bath to 15° C. The precipitated crystals were filtered off and washed with 4×150 ml isopropanol. 218.3 g product were obtained after drying.

R/S-tert-leucinol ratio: 93.7 R: 6.3 S (determined by GC on Lipodex E)

The mother liquor was concentrated to 2000 ml, heated to 45° C. and seeded with a small amount of product at 40° C. The batch was cooled overnight agitation to room temperature, then in an ice/water bath to 15° C. and agitated 4 additional hours. After filtration, washing with isopropanol and drying of the crystals, a further 21.9 g product were isolated.

R/S-tert-leucinol ratio: 88.5 R: 11.5 S (determined by GC on Lipodex E)

The two charges were combined and dissolved in 4000 ml isopropanol at 82° C. After seeding at 78° C., slow crystallization began. The batch was cooled under agitation overnight to room temperature and again cooled in an ice/water bath to 15° C. After 4 h agitation at this temperature the crystals were filtered off and washed in 4 portions with a total of 300 ml isopropanol at 15° C. After drying in a vacuum at 50° C., 210.6 g of the salt of (R)-tert-leucinol and N-(2-naphthoyl)-(S)-tert leucine was obtained (70% yield). A $^1$H-NMR- and an IR spectrum were in accordance with the structure of the product.

Melting range: 184°–189° C. $[\alpha]^{20}_D$: +41.6° (c=1, MeOH)

R/S-tert-leucinol ratio: 98.7 R: 1.3 S (determined by GC on Lipodex E) $C_{23}H_{34}N_2O_4$ calc. C 68.63 H 8.49 N 6.96 (402.52) obs. C 68.48 H 8.75 N 7.00

EXAMPLE 5

Reaction of enriched (S)-tert-leucinol with (S)-mandelic acid

The mother liquor of the fractionated crystallization of example 4 was evaporated in a vacuum to the oil. After it was taken up in 500 ml water, the remaining isopropanol was distilled off and the mixture evaporated to low bulk (500 g). After heating to 55° C. the mixture was adjusted with 6 N hydrochloric acid to pH 5.5, seeded with a small amount of N-(2-naphthoyl)-(S)-tert leucine, and 6 N hydrochloric acid added at 55° C. to attain a pH of 1.8. The mixture was then cooled under agitation to 18° C. at pH 1.35 and filtered. The crystals were washed with water and dried in a vacuum at 75° C. 34.0 g of NMR-spectroscopically pure (2-naphthoyl)-(S)-tert leucine was isolated.

The filtrate was adjusted with sodium hydroxide solution to pH 7.0 and concentrated to 220 g. The mixture was then adjusted with 45 ml of 50% sodium hydroxide solution to pH 13, and after addition of 300 ml toluene heated to 50°–55° C. The aqueous phase was separated, and extraction performed again with 300 ml toluene at 55° C. The combined organic phases were evaporated to 98.2 g (0.82 mole) raw, slightly yellowish tert-leucinol which was heavily enriched with the (S) enantiomer.

The raw amino alcohol was dissolved in 3000 ml isopropanol, filtered and heated to 60° C. After the addition of 114 g (0.75 mole) (S)-mandelic acid, crystallization was initiated by grinding. The mixture was then slowly cooled under agitation, agitated 4 h at 15° C. and filtered. After washing with 400 ml isopropanol at 15° C. and drying the crystals at 50° C. in a vacuum, 157 g product was isolated.

R/S-tert-leucinol ratio: 7.7 R: 92.3 S (determined by GC on Lipodex E)

The product was dissolved in 1560 ml hot isopropanol for recrystallization. After the production of first crystals at 76° C. the mixture was slowly cooled under agitation, agitated 4 h at 15° C., filtered, the product washed with 300 ml isopropanol at 15° C. and dried as above. 140.0 g were isolated.

R/S-tert-leucinol ratio: 3.3 R: 96.7 S (determined by GC on Lipodex E)

Another recrystallization from 1500 ml isopropanol according to the same mode yielded 127.3 g of the salt of (S)-tert-leucinol and (S)-mandelic acid in the form of colorless crystals (63% yield). A $^1$H-NMR- and an IR spectrum were in accordance with the structure of the product.

Melting range: 152°–157° C. $[\alpha]^{20}_D$: +72.6° (c=1, MeOH)

R/S-tert-leucinol ratio: 1.0 R: 99.0 S (determined by GC on Lipodex E)

$C_{14}H_{23}NO_4$ calc. C 62.43 H 8.61 N 5.20 (269.34) obs. C 62.62 H 8.87 N 5.25

EXAMPLE 6

Isolation of (R)-tert-leucinol 201.3 g (0.5 mole) of the salt of (R)-tert-leucinol and N-(2-naphthoyl)-(S)-tert leucine were suspended in 1300 ml water. 50 ml of 37% hydrochloric acid was added dropwise. The mixture was then heated to 50° C., during which a pH of 1.65 developed. The mixture was agitated until the pH remained constant for 15 min and was then cooled to 5° C., during which a pH of 1.05 developed. After 30 min agitation the crystals were filtered off and washed with about 1 l ice water. After drying in a vacuum at 80° C., 141.5 g N-(2-naphthoyl)-(S)-tert-leucine (99% yield) were re-isolated, which were free of impurities according to $^1$H-NMR spectroscopy.

Melting range 161°–162° C. $[\alpha]^{20}_D$: +39.7° (c=1, MeOH) $C_{17}H_{19}NO_3$ calc. C 71.56 H 6.71 N 4.91 (285.33) obs. C 71.32 H 6.79 N 5.11

The filtrate was adjusted to pH 7.5 with 10 M sodium hydroxide solution, evaporated to low bulk in a rotary evaporator to 146 g and divided precisely into two halves. One half was used to produce (R)-4-tert-butyl-2-oxazolidinone (see example 7) and the other half worked up to free (R)-tert-leucinol.

73 g of the above filtrate (containing 0.25 mole (R)-tert-leucinol) was further concentrated to 60 g and adjusted to pH 13.0 with 10 M sodium hydroxide after the addition of 100 ml toluene. After heating to 50° C. the toluene phase was separated and the aqueous phase again extracted at 50° C. with 75 ml toluene. The combined organic phases were dried with sodium sulfate and evaporated to low bulk after filtration to 24.2 g of an almost colorless oil. Distillation yielded 22.9 g (R)-tert-leucinol as colorless, hygroscopic oil which solidified at room temperature (78% yield relative to one half of the salt of (R)-tert-leucinol and N-(2-naphthoyl)-(S)-tert-leucine used). An $^1$H-NMR spectrum corroborated the structure of the product.

Boiling range: 89°–91° C./13 mbar $[\alpha]^{20}_D$: –38.1° (c=2, EtOH) R/S-tert-leucinol ratio: 98.7 R: 1.3 S (determined by GC on Lipodex E)

$C_6H_{15}NO$ calc. C 61.49 H 12.90 N 11.95 (117.19) obs. C 61.48 H 13.64 N 12.07

EXAMPLE 7

Production of (R)-4-tert-butyl-2-oxazolidinone 73 g (containing 0.25 mole (R)-tert-leucinol) of the filtrate cited in example 6 was taken up with 27 ml water and 200 ml toluene. 25 ml (0.26 mole) chloroformic acid ethyl ester were then added dropwise at 20°–25° C., during which the pH was maintained at 7–8.5 by the addition of 10 M sodium hydroxide solution. The mixture was then heated to 60°–65° C. at pH 8.0 and the aqueous phase separated. The toluene phase was dehydrated on a water separator under a slight vacuum and slowly heated after the addition of 0.4 g finely granulated sodium hydroxide at 70° C. A total of 40 ml distillate which contained the ethanol produced during the reaction was separated from 70°–100° C . After cooling of the batch to 65° C. a solution of 0.6 ml glacial acetic acid in 10 ml water was added, the mixture briefly agitated, the aqueous phase separated and the toluene phase compounded again with 15 ml warm water which was separated again after a brief agitation at 65° C. After distilling the organic phase on a water separator the phase was concentrated to 120 ml, filtered hot and slowly cooled off under agitation, during which the product separated in colorless crystals. These crystals were filtered off after 30 min agitation at 5° C., washed with cold toluene and dried in a vacuum at 50° C. 28.6 g (R)-4-tert-butyl-2-oxazolidinone (80% yield) was obtained. A $^1$H-NMR spectrum corroborated the structure of the product.

Melting range: 119°–120° C. $[\alpha]^{20}_D$: +18.8° (c=1, EtOH) R/S-4-tert-butyl-2-oxazolidinone ratio: >99.0 R: <1.0 S (determined by GC on L-Chirasil-Val) $C_7H_{13}NO_2$ calc. C 58.71 H 9.15 N 9.78 (143.19) obs. C 59.04 H 9.56 N 10.05

EXAMPLE 8

Reaction of (RS)-tert-leucinol with N-formyl-(S)-tert-leucine 2.35 g (0.02 mol)(RS)-tert-leucinol and 1.60 g (0.01 mol) N-formyl-(S)-tert-leucine were dissolved in 11 ml warm isopropanol. The batch was then cooled to 5° C., while first crystals formed already at room temperature. The crystals were filtered off and washed with little cold isopropanol 1.23 g crude product (45% yield) were obtained after drying.

R/S-tert-leucinol ratio: 93.9 R: 6.1 S (determined by GC on Lipodex E) 1.12 g (0.004 mol) crude product were dissolved in 9 ml boiling isopropanol. The batch was cooled under agitation to room temperature and agitated for another 2 h. The crystals formed were filtered off and dried in vacuo at 50° C. 0.82 g of the salt of (R)-tert-leucinol and N-formyl-(S)-tert-leucine (73% recrystallization yield, 33% total yield) were obtained.

R/S-tert-leucinol ratio: 98.6 R: 1.4 S (determined by GC on Lipodex E)

References cited herein are hereby incorporated by reference.

What is claimed is:

1. A method of producing optically active tert-leucinol (formula I)

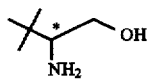

in which * signifies a chirality center, said method comprising converting racemic (RS)-tert-leucinol into a diastereomeric salt pair by reaction with an optically active acid;

removing said salt pair from solution by fractionated crystallization and separating therefrom the optically active acid, thereby releasing the optically active tert-leucinol from said salt pair;

wherein an N-acylated tert-leucine of general formula VIII is used as the optically active acid

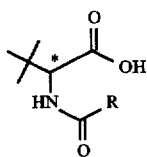

(VIII)

in which R can be hydrogen or an alkyl-, arylalkyl- or aryl group with up to 20 C atoms optionally substituted with or containing heteroatoms, and * signifies a chirality center.

2. The method of claim 1 wherein R contains heteroatoms or is substituted with heteroatoms.

3. The method according to claim 1, wherein optically active N-formyl-tert-leucine is used as the optically active acid.

4. The method according to claim 1, wherein optically active N-(2-naphthoyl)-tert-leucine is used as the optically active acid.

5. The method according to one of claims 1 to 4, wherein an alcohol with 1–6 C atoms is used as solvent for the fractionated crystallization.

6. The method according to claim 5, wherein isopropanol is used as solvent for the fractionated crystallization.

7. A method according to one of claims 1–4 wherein the optically active tert-leucinol is separated from a salt with the optically active acid by reacting the salt with an aqueous solution of a strong acid and recovering the optically active acid by filtering off or by extraction with an organic solvent, subsequently alkalinizing the aqueous solution and extracting the optically active tert-leucinol with an organic solvent.

8. The method according to claim 7, additionally comprising isolating said optically active tert-leucinol by evaporation to low bulk, distillation, chromatography or recrystallization of an acidic salt and further purification.

9. The method according to claim 7, wherein an aromatic hydrocarbon is used as extraction agent for the optically active tert-leucinol.

10. The method according to claim 9, wherein toluene is used as aromatic hydrocarbon.

11. The method according to one of claims 1, 2 or 4 comprising the steps of
i) reacting racemic (RS)-tert-leucinol with N-(2-naphthoyl)-(S)-tert-leucine in a $C_1$–$C_6$ alcohol to obtain the salt of (R)-tert-leucinol and N-(2-naphthoyl)-(S)-tert-leucine in a mother liquor;
ii) separating the salt of (R)-tert-leucinol and N-(2-naphthoyl)-(S)-tert-leucine from the mother liquor;
iii) evaporating said mother liquor to low bulk and taking up said mother liquor in an aqueous, acidic solution, thereby resulting in the precipitation of N-(2-naphthoyl)-(S)-tert-leucine;
iv) filtering off the precipitated N-(2-naphthoyl)-(S)-tert-leucine, thereby obtaining a filtrate containing tert-leucinol which is predominantly the (S) enantiomer;
v) alkalinizing said filtrate and extracting said filtrate with an organic solvent to obtain an extract;
vi) evaporating said extract, taking it up in a lower alcohol and reacting it with (S)-mandelic acid so that the salt of (S)-tert-leucinol and (S)-mandelic acid is obtained.

12. The method according to claim 1 or 2 wherein the racemic (RS)-tert-leucinol is produced by the reduction of trimethylpyruvic acid oxime or an ester of trimethylpyruvic acid oxime.

13. The method according to claim 12, wherein sodium- or lithium boron hydride is used with an activator as reducing agent.

14. The method according to claim 13, wherein hydrogen chloride or sulfuric acid is used as activator.

15. The method according to one of claim 14, wherein the reaction is carried out in a solvent with ether structure.

16. The method according to claim 15, wherein the reaction is carried out between −20° C. and the boiling temperature of the solvent used.

17. The method according to claim 16, wherein the reaction mixture is hydrolyzed after the conclusion of the reaction by adding alcohol and water and optionally an acid, the organic solvent is distilled off, the aqueous phase then made alkaline, the racemic (RS)-tert-leucinol then extracted with an organic solvent and further purified by distillation, chromatography or recrystallization of a salt after evaporation to low bulk.

18. The method according to claim 17, wherein the (RS)-tert-leucinol is extracted with an aromatic hydrocarbon.

19. The method according to claim 18 wherein the aromatic hydrocarbon is toluene.

20. A method of producing 4-tert-butyl-2-oxazolidinone, oxazolines, bicyclic lactams, mercaptophenyloxazoline, bisoxazolines or bis(oxazolinyl)pyridines comprising producing an optically active tert-leucinol according to one of claims 1–19 or one of the salts of optically active tert-leucinol according to one of claims 1–19.

* * * * *